(12) United States Patent
Wallace-Davis et al.

(10) Patent No.: US 7,534,583 B2
(45) Date of Patent: May 19, 2009

(54) ANALYTE MEASUREMENT

(75) Inventors: Emma Naomi Kathleen Wallace-Davis, Oxford (GB); Yann Astier, Oxford (GB)

(73) Assignee: Oxford Biosencors Limited (GB)

( * ) Notice: Subject to any disclaimer, the term of this patent is extended or adjusted under 35 U.S.C. 154(b) by 302 days.

(21) Appl. No.: 10/513,443

(22) PCT Filed: May 16, 2003

(86) PCT No.: PCT/GB03/02150

§ 371 (c)(1),
(2), (4) Date: Nov. 3, 2004

(87) PCT Pub. No.: WO03/097860

PCT Pub. Date: Nov. 27, 2003

(65) Prior Publication Data

US 2005/0164329 A1     Jul. 28, 2005

(30) Foreign Application Priority Data

May 17, 2002   (GB)   ................... 0211449.4

(51) Int. Cl.
*C12Q 1/26*   (2006.01)
(52) U.S. Cl. .................................................. 435/25
(58) Field of Classification Search .............. 205/777.5; 435/25
See application file for complete search history.

(56) References Cited

U.S. PATENT DOCUMENTS

| | | | |
|---|---|---|---|
| 4,783,250 A * | 11/1988 | Pons et al. .................. 204/400 |
| 4,897,173 A | 1/1990 | Nankai et al. |
| 5,100,530 A * | 3/1992 | Dorr et al. .................. 204/406 |
| 5,108,564 A | 4/1992 | Szuminsky et al. |
| 5,206,145 A * | 4/1993 | Cattell ....................... 205/777.5 |
| 5,288,636 A | 2/1994 | Pollmann et al. |
| 5,312,590 A | 5/1994 | Gunasingham |
| 5,413,690 A | 5/1995 | Kost et al. |
| 5,695,947 A | 12/1997 | Guo et al. |
| 5,739,039 A * | 4/1998 | Girault et al. .......... 204/403.14 |
| RE36,268 E | 8/1999 | Szuminsky et al. |
| 5,942,102 A * | 8/1999 | Hodges et al. .............. 205/775 |
| 6,127,127 A * | 10/2000 | Eckhardt et al. ............... 435/6 |
| 6,225,078 B1 | 5/2001 | Ikeda et al. |
| 6,824,669 B1 * | 11/2004 | Li et al. .................... 205/777.5 |

FOREIGN PATENT DOCUMENTS

| | | |
|---|---|---|
| EP | 0 351 891 A2 | 1/1990 |
| EP | 0 849 589 A1 | 6/1998 |
| WO | WO 86/07632 | 12/1986 |
| WO | WO 97/00441 | 1/1997 |
| WO | WO 99/58966 | 11/1999 |
| WO | WO 99/60392 | 11/1999 |
| WO | WO 03/056319 A2 | 7/2003 |

OTHER PUBLICATIONS

J. Christopher Ball, et al., "Electrochemistry in Nanovials Fabricated by Combining Screen Printing and Laser Micromachining," Analytical Chemistry, Feb. 1, 2000, pp. 497-501, vol. 72, No. 3. 2000 American Chemical Society, published on Web Dec. 28, 1999.

Helene Durliat, et al., Spectrophotometric and Electrochemical Determinations of L(+)-Lactate in Blood by Use of Lactate Dehydrogenase from Yeast, Clinical Chemistry, vol. 22, No. 11, p. 1802-1805.

J. Christopher Ball, et al., "Effect of Fabrication Factors on Performance of Screen-Printed/Laser Micromachined Electrochemical Nanovials," Electroanalysis, pp. 685-690, 2000, vol. 12, No. 9.

* cited by examiner

*Primary Examiner*—Maryam Monshipouri
(74) *Attorney, Agent, or Firm*—Quarles & Brady; George E. Haas (57) ABSTRACT

A method for determining the concentration of an analyte in a sample is disclosed which comprises contacting the sample with a micro electrode which comprises an enzyme capable of reacting with said analyte and a redox mediator which is capable of being converted by being oxidised or reduced by said enzyme once the latter has reacted with the analyte, allowing the analyte to react with the enzyme, then applying a potential across the electrode and measuring the resulting concentration of the converted mediator electrochemically.

25 Claims, 5 Drawing Sheets fig. 1 fig 2 fig 3

ANALYTE MEASUREMENT

CROSS REFERENCE TO RELATED APPLICATIONS

This application claims priority of International Patent Application No. PCT/GB03/02150 filed on May 16, 2003.

Statement Regarding Federally Sponsored Research Or Development

Not Applicable

BACKGROUND OF THE INVENTION

1. Field of the Invention

This invention relates to a method for determining the concentration of an analyte in a sample and, in particular, to a method for determining the concentration electrochemically.

2. Description of the Related Art

It is particularly valuable to determine the concentration of a specific component in a sample which is of biological origin, for example blood. For this purpose a biosensor is used; use is made of a change in the oxidation state of a mediator which interacts with an enzyme which has reacted with the analyte to be determined. The oxidation state of the mediator is chosen so that it is solely in the state which will interact with the enzyme on addition of the substrate. The analyte reacts with a stoichiometric concentration of the mediator via enzyme. This causes the mediator to be oxidised or reduced (depending on the enzymatic reaction) and this change in the level of mediator can be measured by determining the current generated at a given potential.

Normally, a measurement is taken during the oxidation (or reduction) of the mediator by the enzyme as it reacts with the analyte. This can, though, give rise to unreliable results. It has been proposed, therefore, to wait for the reaction to go to completion and then to take a measurement. However, the value obtained changes with time such that it is generally necessary to take a number of readings and then to determine the concentration using either an algorithm or by integration of the area under the curve which corresponds to the plot of the values. This change in value is caused by the effect of diffusion which occurs essentially linearly from the electrode. Thus as some of the mediator is oxidised (or reduced) on the electrode more mediator diffuses to the electrode on a continuing basis. However, this linear diffusion results in depletion of electroactive material around the working electrode.

In order to determine the concentration it is necessary to first of all obtain a value in the absence of the analyte and to subtract this "background" value from the enhanced value which one obtains when the analyte is present. It will be appreciated that this procedure is both complicated and prone to error.

Recently, steps have been taken to reduce the size of biosensors by making use of a micro electrode. This can be defined as an electrode where at least one of the dimensions does not exceed 50 µm and is frequently 1 to 25 or 30 µm.

Micro electrodes were devised because they were perceived to be better for the measurement of very small currents. This is because the use of an array of micro electrodes gives a better signal to noise ratio than does a single electrode. Micro electrodes were therefore devised for direct current determination and they have not found utility as biosensors involving an enzyme and a mediator. It has, though, surprisingly been found that the use of a micro electrode can, if used in a particular way, overcome the disadvantages of macro electrodes.

That micro electrodes can be used for this purpose is particularly surprising for two principal reasons. First, the current enhancement due to the presence of the analyte over the background level for a micro electrode is of course very much smaller than for a macro electrode. Accordingly with decreasing size it is impossible to obtain any accurate measurements. Second, because the area of the electrode is very small in relation to the volume of the sample diffusion to the electrode surface no longer takes place linearly as with macro electrode but, rather, radially. The distance over which the reaction occurs in solution is large compared to the size of the micro-electrodes such that one would expect there to be little or no catalytic enhancement. One would therefore expect with decreasing electrode size no meaningful measurement to be obtainable.

Under normal steady-state conditions, the average distance that the oxidised state of the mediator will diffuse before it reacts to reform the reduced state will be $(Dt_L)^{1/2}$ where D is the diffusion coefficient of the oxidised state and $t_L$ is the reaction half life before the oxidised state is reformed. It will be appreciated that because the size of the micro electrode is small in comparison to this diffusion distance, there is normally very little current enhancement in the presence of the catalytic reaction. In other words, the presence of the analyte which promotes the catalytic reaction leads to only a small current increase above that initially present. The small magnitude of this "perturbation current" thus means that accurate analytical results cannot be obtained.

SUMMARY OF THE INVENTION

Figure 1:
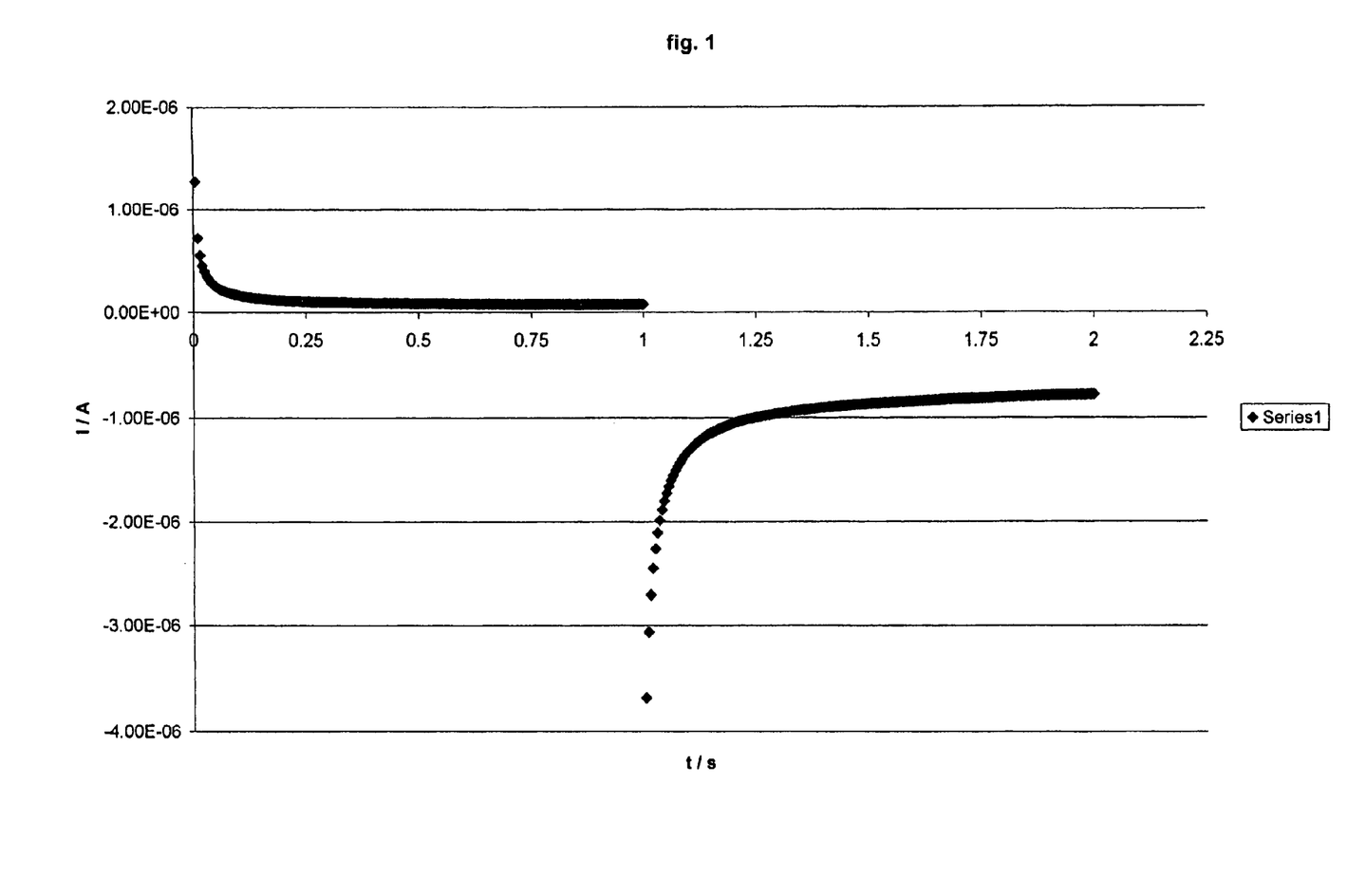
FIG. 1 displays the current response during the double potential step experiments. The value of the current is seen to become constant within about 400 msec from the potential step. The current values for the oxidation step and the reduction currents are read from the plot 400 msec after the first and the second potential step respectively.
Figure 2:
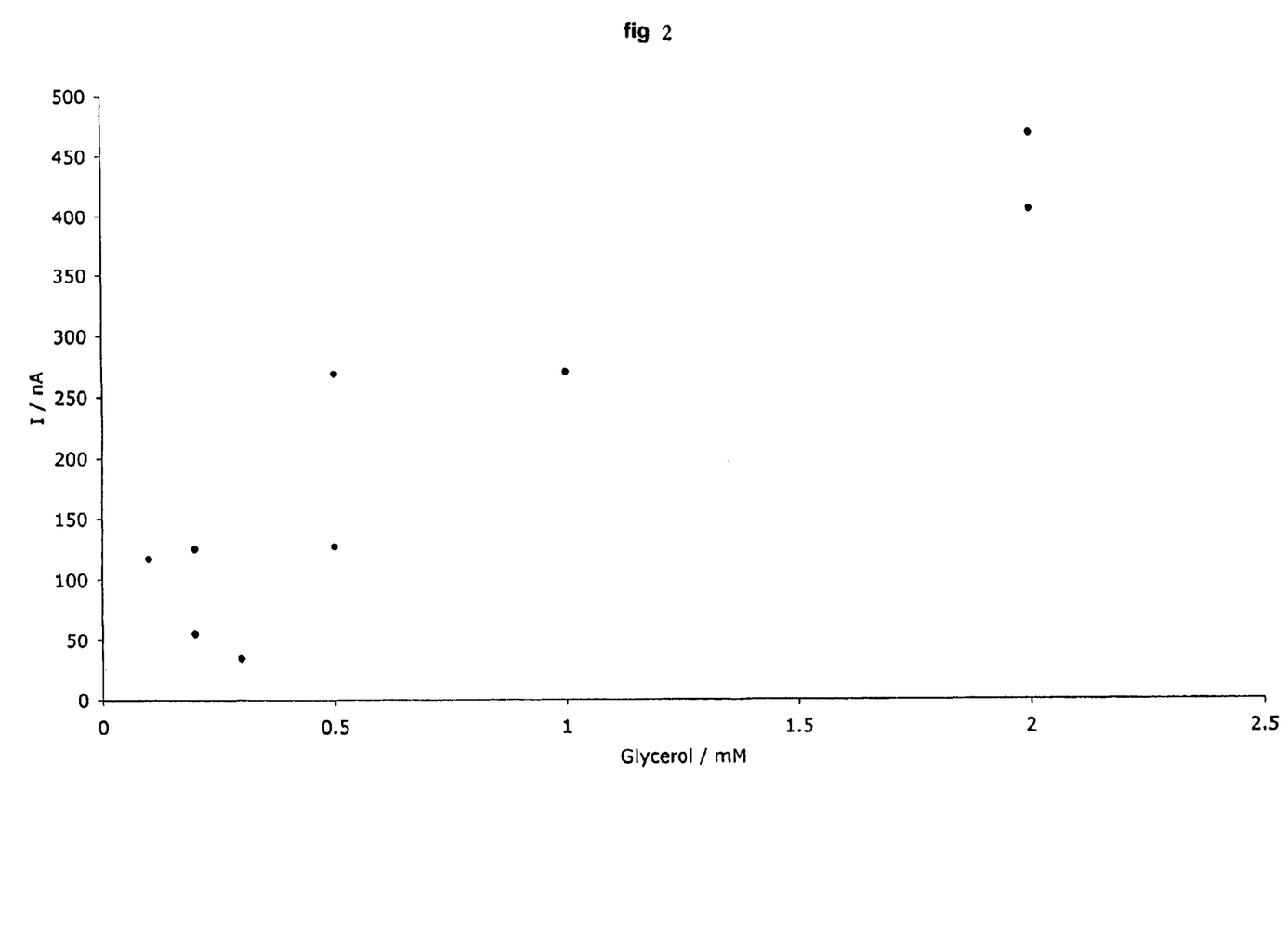
FIG. 2 shows oxidation currents i.e. from the first potential step only, plotted against glycerol concentrations. These currents are subject to electrode area variability.

Despite these significant drawbacks it has surprisingly been found that if the determination is made after the reaction has taken place the shape of the potential curve after an initial peak is substantially horizontal with the result that, firstly, a direct measurement can be obtained without any need for subtraction for the background and that, secondly, only one measurement is required. FIG. 1 illustrates a typical curve which can be obtained. In other words, the concentration can be determined directly from a single value.

According to the present invention there is provided a method for determining the concentration of an analyte in a sample which comprises contacting the sample with a micro electrode which comprises an enzyme capable of reacting with said analyte and a redox mediator which is capable of being converted by being oxidised or reduced by said enzyme once the latter has reacted with the analyte, allowing the analyte to react with the enzyme, then applying a potential across the electrode, and measuring the resulting concentration of the converted mediator electrochemically. Typically, the resulting current can be measured and the concentration determined directly by comparison to a stored reference data set. A catalytic current is generated as the enzyme continually turns over the substrate and the enzyme is continually reused. According to the present invention, the reaction goes to completion or reaches a stable equilibrium state which might be less than 100% conversion and could be as little as, say, 50% conversion before the potential is applied; the drive to complete the reaction arises from the vast excess of the enzyme in this system—many orders of magnitude bigger than in the catalytic system.

It will be appreciated that with such a method reaction within the mediator occurs throughout the solution, the mediator reacts with the enzyme and when the voltage is applied the resulting oxidised/reduced mediator is reduced/oxidised to its original oxidation state at the electrode. This is in contrast to a catalytic system where the mediator is oxidised/reduced and this then reacts with the enzyme—a catalytic amount is obtained with a low level of enzyme throughout the solution is due to continued turnover. It follows that in the system of the present invention the enzyme should be in excess throughout the whole of the solution which is under test. In contrast in the normal catalytic system as the reaction is confined to the solution adjacent to the electrode surface the bulk of the test solution is unperturbed by the enzymatic reaction. It should be noted this requirement does not necessarily mean that the enzyme has to be homogenous through the mixture. Practically it has been found that the enzyme excess should desirably be such that the predicted reaction time is an order of magnitude lower than the acceptable measurement time for the sensor. Hence the required amount of enzyme dried on a strip (which will be related to the wet-up time) will be dictated by the required response time, the rate of enzyme re-suspension along with the amount of activity retained by the enzyme, the volume in which the test is being completed and the maximum concentration of analyte to be tested. Clearly these parameters will vary from test to test and enzyme to enzyme. For example, if the enzyme has an activity of 1000 U/mg, the reaction volume is 10 µL, the required response time is 10 seconds, 50% of the enzyme activity is recovered on re-suspension and the maximum analyte concentration is 1 mM, then 2 U/ml are required in the deposition solution. It will be appreciated that the reacted mediator is present at a concentration corresponding to an electron ratio of 1:1 with the analyte.

Conventional microelectrodes, typically with a working electrode and a reference electrode can be used in the method of the present invention so that a detailed discussion of them is unnecessary. In a preferred embodiment the working electrode is in a wall of the receptable forming the micro electrode as disclosed in British Application No. 0130684.4, to which reference should be made for further details. Likewise the usual enzymes and mediators can be employed. Typical mediators thus include ferricyanide, phenazine alkoxysulphates such phenazine ethosulphate and phenazine methosulphate and substituted phenazine alkoxysulphates including 1-methoxy phenazine methosulphate along with phenylene diamine and ruthenium compounds such as ruthenium hexamine. Suitable enzymes which can be used will, of course, depend on the analyte and on the mediator. By way of example, suitable enzymes which can be used with ferricyanide include glucose dehydrogenase (for glucose), cholesterol esterase, horseradish peroxidase, cholesterol dehydrogenase and cholesterol oxidase for cholesterol, lipo protein lipase, glycerol kinase and glycerol-3-phosphate oxidase for triglycerides, lactate oxidase and lactate dehydrogenase for lactate as well as diaphorase. The normal stabilisers for the enzymes such as BSA (bovine serum albumen) as well as non-ionic polyol surfactants such as those known under the trade mark Triton X and cholic acid and other bile acid salts can be used. Typically the mediator is used in a concentration from 0.01 to 1 molar, such as 0.05 to 0.25 molar while the concentration of enzyme is typically 10 to $10^6$ U/ml, for example 100 to 10,000 U/ml. The mediator should normally be in excess in relation to the analyte. Desirably the pH is controlled by the addition of buffers such as potassium phosphate so that the pH is maintained at the optimum level for the particular analyte under test. Other buffers which can be used include sodium phosphate, Goods buffer, tris(hydroxymethyl)aminomethane (Tris), citrate/phosphate, 3-morpholinopropanesulfonic acid (MOPS), 2-morpholinoethanesulfonic acid (MES), N-2-hydroxyethyl piperazine (HEPES), tricine, bicine, piperazine-N,N'-bis(2-ethane sulfonic acid) (PIPES), N-tris(hydroxymethyl)methyl-2-aminoethane sulfonic acid (TES), 3-cyclohexylamino)-1-propanesulfonic acid (CAPS) and [(2-hydroxy-1,1-bis[hydroxymethyl]ethyl)amino]-1-propanesulfonic acid (TAPS) as well as other biological buffers.

The micro electrodes typically comprise a working electrode and a counter electrode as well as a reference electrode. In some cases the counter electrode and the reference electrode are combined. The working electrode is typically made of palladium, platinum, gold or carbon. The counter electrode is typically carbon, Ag/AgCl, Ag/Ag$_2$SO$_4$, palladium, gold, platinum, Cu/CuSO$_4$, Hg/HgO, Hg/HgCl$_2$, Hg/HgSO$_4$ or Zu/ZuSO$_4$.

When enzymes are deposited on a surface such as an electrode they have a tendency to both denature and to form relatively insoluble "masses". Typically, the enzyme solution is dried on the sensor and, accordingly, these issues need to be addressed to ensure the enzyme retains its activity and that it re-suspends within a reasonable timescale. It has been found that this reaction can be assisted by depositing the enzyme solution on the electrode in the presence of salt such as a chloride or sulphate wherein the cation is typically potassium, ammonium, or magnesium such as potassium and magnesium chloride and ammonium sulphate, or detergent such as those known under the trade mark Triton X e.g. Triton X-100 or sodium deoxycholate and similar bile acid salts, SDS, 3-[(3-cholamidopropyl)dimethylammonio]-2-hydroxy-1-propanesulfonate (CHAPSO), 3[(3-cholamidopropyl)dimethylammonio]propanesulfonic acids (CHAPS), octylglucopyranoside, octylthiogluconpyranoside and various other polyols, polyvinylalcohol (PVA), polyethylene glycol (PEG), carboxymethyl cellulose, dextran sulphate, hydroxypropylmethyl cellulose, starch, n-dodecyl maltoside, ethyl cellulose and polymethacrylic acid or microcrystals such as sepharose, Sephadex G25. Alternatively, one or more of these components can be applied to the electrode surface first and then dried before the enzyme solution is applied.

In a typical measurement, after the sample has been applied to the micro electrode a time (SD) of, for example, 0.1 or 1 to 180, preferably 0.1, 0.5 or 1 or even 10 to 60, more preferably 0.1 to 60, especially 0.5 to 20, in particular about 20 seconds, is set during which all the electrodes are held at earth potential i.e. no current flows. This is to allow time for the enzyme to re-suspend, to substantially react fully (or reach a stable equilibrium state) with the analyte and for the electrodes and enzyme to become fully wetted. A potential, typically from −2 to +2V, e.g. from −1 to +1V, for example about 0.5V, depending on the enzyme system employed is then applied to the electrode and this determines the amount of mediator stochiometrically turned over by the enzyme. A time delay (D1), typically of 10 to 500 milliseconds and generally no more than 1 or 5 seconds, is made prior to making a measurement. Typically the measurement (C1) is the current response. After this time delay the current is measured. It will be appreciated that there is no need to know the measurement when the potential is first applied.

The device can be calibrated beforehand with given concentrations of analyte so that a direct reading can be obtained. It has been found to be that the current obtained is proportional to the concentration of the analyte.

Although a single reading is all that is necessary, in general it is desirable that more than one reading, for example 10 to 100 readings at a sample state of, say, 25 to 1000 Hz, is obtained in order to eliminate error and obtain an average value. It is important to stress, though, that these multiple readings are taken purely for averaging purposes in contrast to the situation when using a macro electrode where multiple readings are essential in order to obtain a concentration value by means of integration or a specific algorithm.

It has been found, though, that there is a difficulty in pre-calibrating a micro electrode even, though, ostensibly it is made to be identical to a previous micro electrode. In other words the pre-calibration of the previous micro electrode cannot be used accurately for the subsequent micro electrode. Because of the small sizes involved it is very difficult to ensure that the area of the electrode, which does, of course, critically determine the current which is obtained, is precisely the same from one micro electrode to the next. Use of the area compensation technique will eliminate errors induced due to different electrode sizes in the short timescale regime. Differences in electrode area will also result in the smaller areas reaching a quasi-steady state faster than the relatively larger areas. This variation will be apparent in the relative increase in magnitude of the electrochemical response. In the case of the current response; this is exacerbated if the system is operated at short timescale by the current due to planar diffusion adding to the quasi-steady state current but will frequently be apparent also at longer timescales when the electrodes have reached a steady rate.

The use of an independent calibration sample is useful in this regard and also to eliminate any differences arising out of changes in the wetting-up volume. Under some circumstances it may be best to add a separate redox probe as a calibrator; judicious choice of this probe is essential to ensure that (a) the initial redox state of the probe is such that it is thermodynamically unfavourable for it to react with any redox state of the mediator (b) any reaction between any subsequent redox state of the redox probe and the mediator is too slow to observe on the timescale of our measurement.

Figure 3:
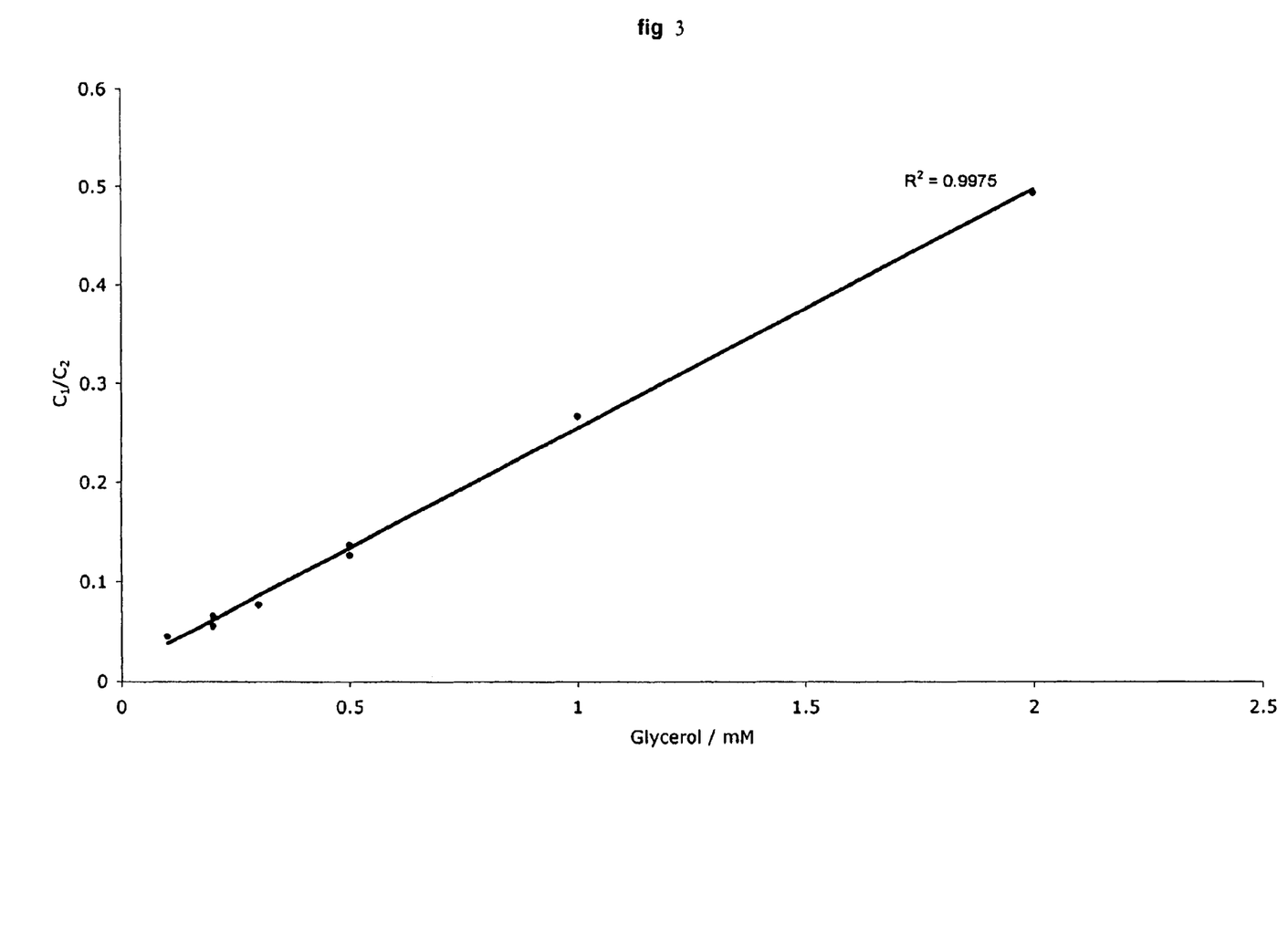
FIG. 3 is a plot of ratios obtained from the oxidation currents displayed in FIG. 2, divided by their respective reduction currents obtained from the second potential step (as shown in FIG. 1). These ratios are the result of an area compensation and prove to be linear with glycerol concentration.

According to a particular aspect of the present invention, a means has been found of eliminating any error due to differences in the area of the electrode. This involves a particular method of working. For an amperometric measurement, effectively after the measurement has been obtained (i1) as described above, for example after a time delay of, say, 10 to 500 milliseconds, as before, the potential is reversed so that the mediator which has been oxidised by the reaction is then reduced and another value (C2) of the current obtained (i2), typically after a similar time delay (D3). It will be appreciated that in each case the current obtained is proportional to the area of the electrode surface so that by obtaining a ratio of the two currents (i1/i2) or a percentage of the first current in relation to the sum of the two currents (i1/i1+i2) a value can be obtained which is independent of the surface area of the electrode FIG. 3 illustrates, diagrammatically, the procedure. This ratio or percentage can therefore be read off directly from a calibration curve in exactly the same way as if a single measurement is obtained. For a voltametric measurement using a given redox couple, a second non-reactive redox couple can be used; it is important that the relative concentration of the two redox couples remain constant across all the electrodes under test.

This compensation method of working is, therefore, of particular value in eliminating differences in the surface area of micro electrodes being produced, typically as biosensors. Since the observed current is a linear combination of planar and 'radial' diffusion the use of the ratio technique can eliminate changes in relative percentages of these two components resulting from the different electrode sizes.

Accordingly, the present invention also provides a method for determining the concentration of an analyte in a sample which comprises contacting the sample with a micro electrode which contains an enzyme capable of reacting with said analyte and a redox mediator which is capable of being converted by being oxidised or reduced by said enzyme once the latter has reacted with the analyte, allowing the analyte to react with the enzyme, then applying a potential across the electrode, measuring the resulting current, reversing the potential and measuring the current again, expressing the two currents as a ratio or a percentage and determining the concentration of the analyte directly therefrom.

In order to simplify the operation, the present invention also provides a micro electrode comprising a working electrode and a counter electrode, means for applying a positive or negative potential across the electrode at a given time after the sample has been applied to it, means for determining the resulting current at a set time of no greater than 1 second, e.g. from to 500 milliseconds, thereafter, means for reversing the potential across the electrode and determining the resulting current at said set time after the reversal. It will be appreciated that the various means can be provided by a single processor/microchip.

The following Examples further illustrate the present invention. The following sensors have been used:

Cholesterol Oxidase Sensor:
Horseradish peroxidase @ 400 U/mL
Cholesterol oxidase @ 700 U/ml
Cholesterol esterase @ 700 U/ml
0.08 M potassium ferricyanide
0.1 M potassium chloride
0.1 M potassium phosphate, pH 7.4
100 g/dm$^{-3}$ Triton-X 100
0.2 gm mL Sephadex G25

Triglyceride Sensor:
Glycerol phosphate oxidase @ 4500 U/mL
Glycerol kinase @ 4500 U/mL
Lipase @ 100000 U/mL
0-2 M potassium chloride
0.2 potassium ferricyanide
0.025 M adenosine triphosphate
0.002 M ammonium sulphate
0.002 M magnesium chloride
0.1 g/mL Sephadex G25

If plotted against glycerol concentration, the first oxidative current depends on enzyme turnover but also on electrode surface area. Because disposable microelectrodes tend to have variable surface areas, the relation between oxidation current and glycerol concentration is compromised.

On the other hand, by dividing the oxidation current from the first potential step by the reduction current from the second potential step, a unitless ratio is obtained which eliminates the electrode area factor.

DETAILED DESCRIPTION OF THE INVENTION

EXAMPLE 1

Measurements were made on an electrodes of the type disclosed in British application no. 0130684.4. The working electrodes were Coates carbon printed onto a 250 μm melonex upper substrate. This was adhered to a 125 μm melonex lower substrate in order to form the well. Ag/AgCl were printed onto the upper substrate. The components of the biosensor coating solution (concentrations) were hexaammineruthenium (III) chloride (4.8 mM), NAD+ (0.8 mM), PdR (1.6 μM), polymeric detergent (2.5 mM) and glucose dehydrogenase (1 U/biosensor).

Figure 4:
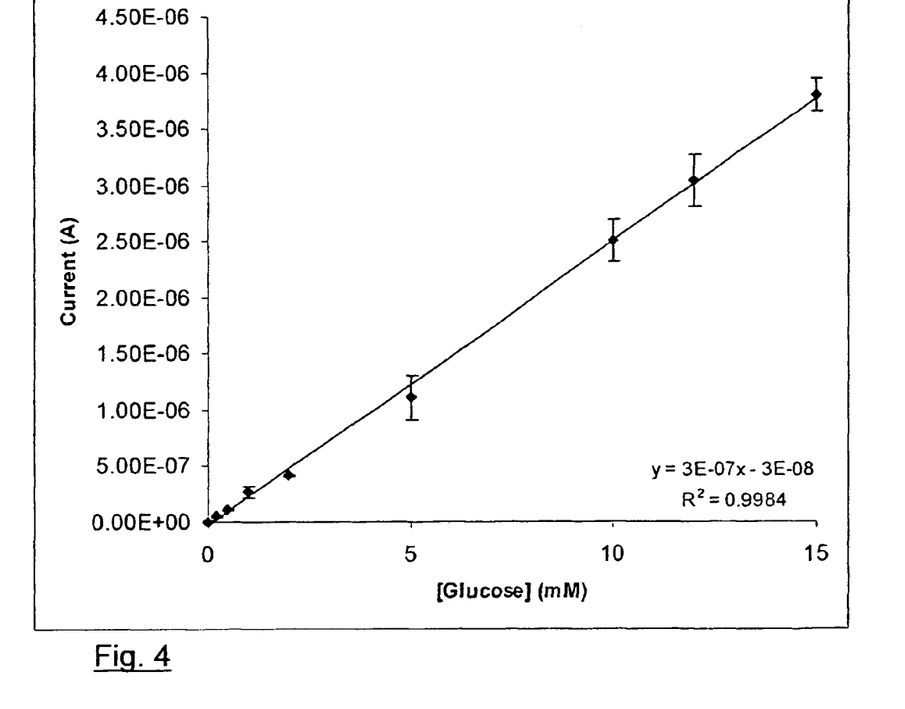
FIG. 4 shows oxidation currents plotted against glucose concentrations using the specific system described in Example 1.

The supporting electrolyte was 0.1M, pH 7.4 phosphate. A potential of +0.2V versus Ag/AgCl was applied and measurements were taken 0.5 s after the application of the potential. The results obtained are shown in FIG. 4.

EXAMPLE 2

Electrodes were constructed as in Example 1 from a 250 μm PET layer on which a 7 μm Coates carbon ink layer has been screen-printed followed by a 30 μm Dupont 5036 dielectric layer. This layer has been punched to produce a 1 mm diameter hole and has then been adhered to a 125 μm PET base layer using pressure sensitive lamination, with a common Ag/AgCl (using Ercon E0430-128) counter reference on the top of the strip.

Amperometric current was measured 1 second after the application 0.15 V followed by the application of −0.45 V vs. Ag/AgCl on the addition of varying amounts of LDL cholesterol in 0.1 mol dm$^{-3}$ Tris buffer at pH 7.4 containing 0.1 mol dm$^{-3}$ KCl to electrodes on which 0.3 μL of a solution containing NAD (0.022 g/ml, ruthenium hexaamine @ 0.021 g/ml, cholesterol esterase @ 1.25 kU/ml, cholesterol dehydrogenase @ 4.2 kU/ml, putidaredoxin reductase @ 650 kU/ml, 0.1 M KCL, 0.1 M Tris-HCl @ pH 9 octylglucopyranoside @ 100 g/dm$^{-3}$ has been dried.

The results obtained are given in the following table:

| LDL/mM | Without area compensation | | With area compensation | |
|---|---|---|---|---|
| | Current/nA | % CV | Ratio | % CV |
| 1 | 285 | 15 | 5.36 | 0.6 |
| 3 | 354 | 13 | 8.33 | 2.8 |
| 5 | 691 | 10 | 15.3 | 6.3 |

It can be seen that the use of area compensation decreases the magnitude of the error and is therefore extremely useful in the production of accurate sensors.

EXAMPLE 3

Electrodes were constructed as in Example 1 from a 250 μm PET layer on which a 20 μm Coates 268203 carbon ink layer had been screen-printed, followed by a 30 μm Ronseal dielectric layer. This layer has been punched to produce a 1 mm diameter hole and has then been adhered to the PET base layer using 7841 sheet adhesive, with a common Ag/AgCl (Ercon E0430-128) counter reference on the top of the strip.

Amperometric current was measured 1 second after the application of 0.20V vs. Ag/AgCl on the addition of 2, 5, 7.5, 10, 12.5 and 15 mmol dm$^{-3}$ glycerol in 0.1 mmol dm$^{-3}$ Tris buffer at pH 9, containing 0.1 mol dm$^{-3}$ KCl and 1% OGP, to electrodes on which 0.3 μL of a solution containing 0.1 mol dm$^{-3}$ ruthenium hexamine, 0.15 mol dm$^{-3}$ ammonium sulfate, 0.04 mol dm$^{-3}$ NAD, 150 U/mL glycerol dehydrogenase and 6.7 kU/mL diaphorase have been dried.

The results obtained are shown in the following table:

| [Glycerol]/mM | Oxidation Current, nA | Reduction current, nA | Ratio |
|---|---|---|---|
| 2.0 | 95 | −3815 | 2.50 |
| 5.0 | 167 | −3772 | 4.42 |
| 5.0 | 185 | −3776 | 4.91 |
| 7.5 | 177 | −2288 | 7.75 |
| 7.5 | 192 | −2827 | 6.80 |
| 7.5 | 163 | −2426 | 6.70 |
| 7.5 | 224 | −3217 | 6.97 |
| 10.0 | 343 | −3769 | 9.10 |
| 12.5 | 226 | −2098 | 10.77 |
| 12.5 | 283 | −2400 | 11.80 |
| 12.5 | 233 | −2358 | 9.90 |
| 12.5 | 277 | −2888 | 9.59 |
| 15.0 | 433 | −3582 | 12.09 |

EXAMPLE 4

Electrodes were constructed as in Example 1 from a 250 μm PET layer on which a 7 μm Coates carbon ink 268203 layer has been screen-printed followed by a 30 μm Dupont 5036 dielectric layer. This layer has been punched to produce a 1 nm diameter hole and has then been adhered to a 125 μm PET base layer using pressure sensitive lamination, with a common Ag/AgCl (using Ercon E0430-128) counter reference on the top of the strip.

Amperometric current was measured 1 second after the application 0.15 V followed by the application of −0.45 V vs. Ag/AgCl on the addition of 1, 3, 5 mmol dm$^{-3}$ LDL cholesterol in 0.1 mol dm$^{-3}$ Tris buffer at pH 7.4 containing 0.1 mol dm$^{-3}$ KCl to electrodes on which 0.3 μL of a solution containing NAD @ 0.022 g/ml, ruthenium hexaamine @ 0.021 g/ml, cholesterol esterase @ 1.25 kU/ml, cholesterol dehydrogenase @ 4.2 kU/ml, putidaredoxin reductase (650 kU/ml, 0.1 M KCL, 0.1 M Tris-HCl (pH 9 octylglucopyranoside @ 100 g/dm$^{-3}$ has been dried.

Figure 5:
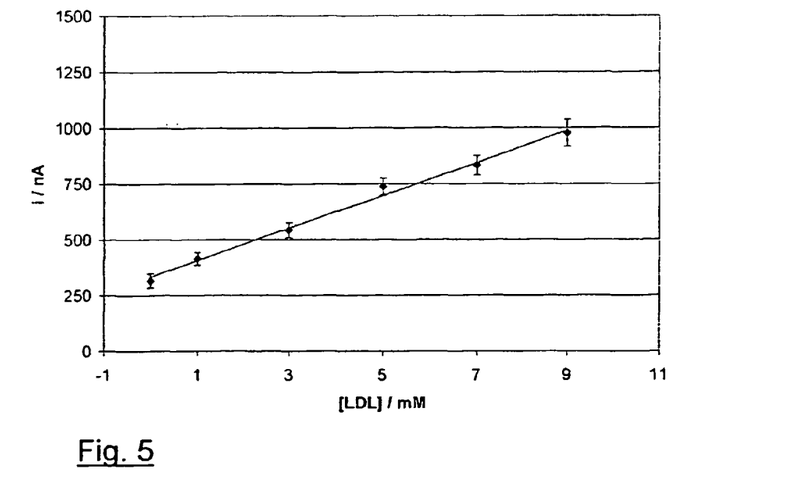
FIG. 5 shows oxidation currents plotted against LDL cholesterol concentrations using the specific system described in Example 4.

The results obtained are shown in FIG. 5.

EXAMPLE 5

Electrodes were constructed as in Example 1 from a 250 μm PET layer on which a 15 μm Coates carbon ink 26-8203 layer has been screen-printed followed by a 30 μm Ronseal layer. This layer has been punched to produce a 1 mm diameter hole and has then been adhered to a 125 µm PET base layer using ARcare 7841 sheet adhesive, with a common Ag/AgCl counter reference on the top of the strip.

Cyclic voltammetric current was measured at 0.15 V vs. Ag/AgCl immediately after addition of 2, 4, 6, 8 and 10 mmol $dm^{-3}$ NADH in 0.1 mol $dm^{-3}$ Tris buffer at pH 9 containing 0.1 mol $dm^{-3}$ KCl to electrodes on which 0.2 µL of a solution containing 0.2 mol $dm^{-3}$ ruthenium hexaamine and 650 KU/mL putidaredoxin reductase has been dried.

Figure 6:
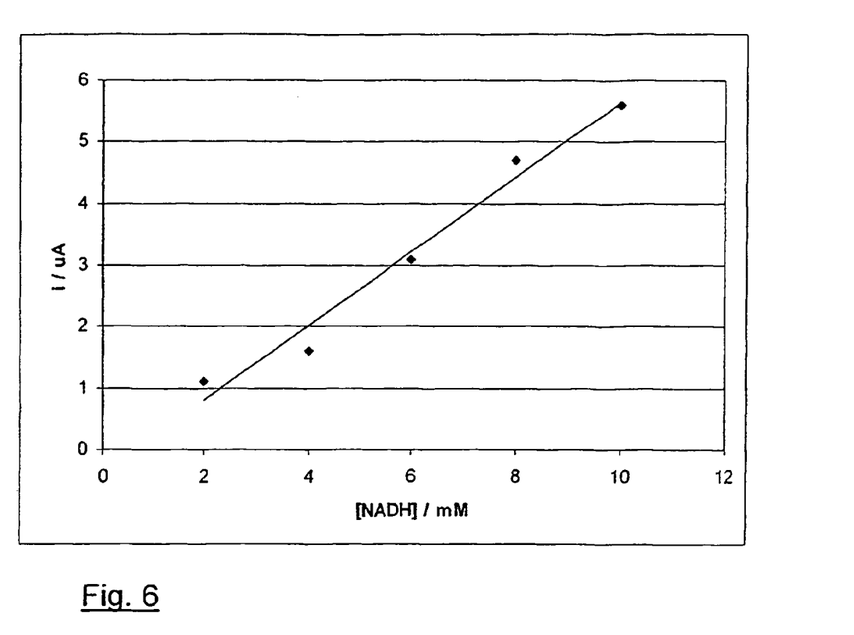
FIG. 6 shows oxidation currents plotted against NADH concentrations using the specific system described in Example 5.

The results obtained are shown in FIG. 6.

EXAMPLE 6

Electrodes were constructed as in Example 1 from a 250 µm PET layer on which a 15 µm Coates carbon ink 26-8203 layer has been screen-printed followed by a 30 µm Ronseal layer. This layer has been punched to produce a 1 mm diameter hole and has then been adhered to a 125 µm PET base layer using ARcare 7841 sheet adhesive, with a common Ag/AgCl counter reference on the top of the strip.

Amperometric current was measured 1 second after the application 0.15 V vs. Ag/AgCl on the addition of 2, 4, 6, 8 and 10 mmol $dm^{-3}$ NADH in 0.1 mol $dm^{-3}$ Tris buffer at pH 9 containing 0.1 mol $dm^{-3}$ KCl to electrodes on which 0.2 µL of a solution containing 0.2 mol $dm^{-3}$ ruthenium hexaamine and 650 KU/mL putidaredoxin reductase has been dried.

Figure 7:
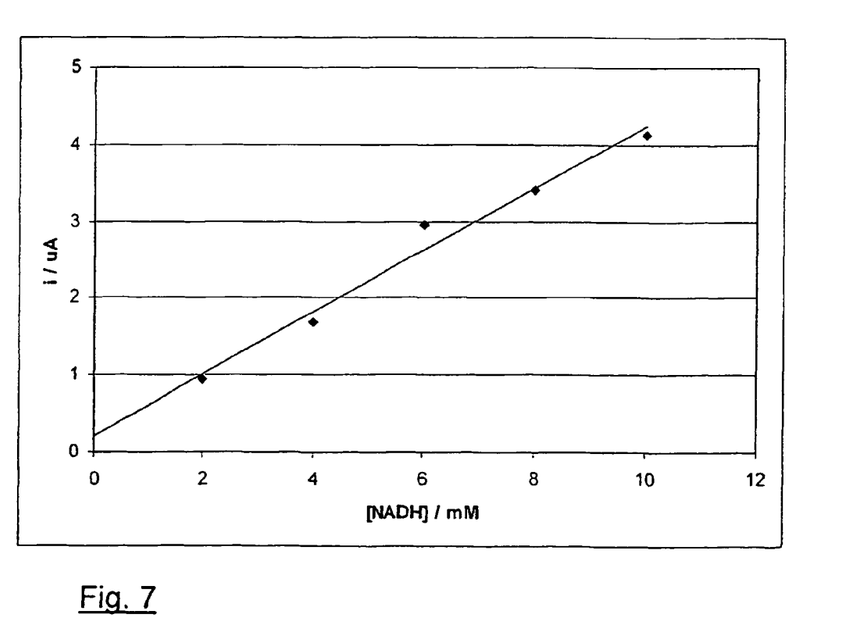
FIG. 7 shows oxidation currents plotted against NADH concentraions using the specific system described in Example 6.

The results obtained are shown in FIG. 7.

The invention claimed is:

1. A method for determining the concentration of an analyte in a sample which comprises contacting the sample with a micro electrode which comprises an enzyme capable of reacting with said analyte and a redox mediator which is capable of being converted by being oxidised or reduced by said enzyme once the latter has reacted with the analyte, allowing the analyte to react with the enzyme, said reaction going to completion or substantially to completion before a potential is applied, then applying a potential across the electrode and measuring the resulting concentration of the converted mediator electrochemically.

2. A method according to claim 1 wherein the resulting concentration is measured from the resulting current.

3. A method according to claim 1 wherein the micro electrode comprises a working electrode, a counter electrode and a reference electrode.

4. A method according to claim 3 wherein the counter electrode and reference electrode are combined.

5. A method according to claim 3 wherein the working electrode is made of palladium, platinum, gold or carbon and the counter electrode is made of carbon, Ag/AgCl, $Ag/Ag_2SO_4$, palladium, gold, platinum, $Cu/CuSo_4$, Hg/HgO, $Hg/HgCl_2$, $Hg/HgSO_4$, or $Zu/ZuSO_4$.

6. A method according to claim 1 wherein the mediator is ferricyanide, phenazine ethosulphate, phenazine methosulphate, 1-methoxy phenazine methosulphate, phenylene diamine or ruthenium hexamine.

7. A method according to claim 1 wherein the enzyme is glucose dehydrogenase, cholesterol esterase, horseradish peroxidase, cholesterol dehydrogenase, cholesterol oxidase, lipo protein lipase, glycerol kinase, glycerol dehydrogenase, glycerol-3-phosphate oxidase, lactate oxidase or lactate dehydrogenase.

8. A method according to claim 1 which comprises allowing a time of 0.5 to 180 seconds to elapse after the sample has been applied to the micro electrode before applying a potential across the electrode and making an electrochemical measurement no more than 5 seconds thereafter.

9. A method according to claim 8 wherein the potential applied is from −2 to +2 volt.

10. A method according to claim 8 wherein the measurement is taken 10 to 500 milliseconds after the potential has been applied.

11. A method according to claim 8 wherein 10 to 100 measurements are taken.

12. A method according to claim 1 wherein the micro electrode has previously been calibrated to provide a direct reading.

13. A method according to claim 1 wherein the mediator is present in excess in relation to the analyte.

14. A method of determining the concentration of an analyte in a sample which comprises contacting the sample with a micro electrode which contains an enzyme capable of reacting with said analyte and a redox mediator which is capable of being converted by being oxidised or reduced by said enzyme once the latter has reacted with the analyte, allowing the analyte to react with the enzyme, then applying a potential across the electrode, measuring the resulting current, reversing the potential and measuring the current again, expressing the two currents as a ratio or a percentage and determining the concentration of the analyte directly therefrom.

15. A method according to claim 14 wherein the micro electrode comprises a working electrode, a counter electrode and a reference electrode.

16. A method according to claim 15 wherein the counter electrode and reference electrode are combined.

17. A method according to claim 15 wherein the working electrode is made of palladium, platinum, gold or carbon and the counter electrode is made of carbon, Ag/AgCl, $Ag/Ag_2SO_4$, palladium, gold, platinum, $Cu/CuSo_4$, Hg/HgO, $Hg/HgCl_2$, $Hg/HgSO_4$, or $Zu/ZuSO_4$.

18. A method according to claim 14 wherein the mediator is ferricyanide, phenazine ethosulphate, phenazine methosulphate, 1-methoxy phenazine methosulphate, phenylene diamine or ruthenium hexamine.

19. A method according to claim 14 wherein the enzyme is glucose dehydrogenase, cholesterol esterase, horseradish peroxidase, cholesterol dehydrogenase, cholesterol oxidase, lipo protein lipase, glycerol kinase, glycerol dehydrogenase, glycerol-3-phosphate oxidase, lactate oxidase or lactate dehydrogenase.

20. A method according to claim 14 which comprises allowing a time of 0.5 to 60 seconds to elapse after the sample has been applied to the micro electrode before applying a potential across the electrode and making an electrochemical measurement no more than 5 seconds thereafter.

21. A method according to claim 20 wherein the potential applied is from −2 to +2 volt.

22. A method according to claim 20 wherein the measurement is taken 10 to 500 milliseconds after the potential has been applied.

23. A method according to claim 20 wherein 10 to 100 measurements are taken.

24. A method according to claim 14 wherein the micro electrode has previously been calibrated to provide a direct reading.

25. A method according to claim 14 wherein the mediator is present in excess in relation to the analyte.

* * * * *

UNITED STATES PATENT AND TRADEMARK OFFICE
CERTIFICATE OF CORRECTION

PATENT NO. : 7,534,583 B2  
APPLICATION NO. : 10/513443  
DATED : May 19, 2009  
INVENTOR(S) : Emma N. K. Wallace-Davis et al.

Page 1 of 1

It is certified that error appears in the above-identified patent and that said Letters Patent is hereby corrected as shown below:

In Column 4, line 4 "(TES), 3-cyclohexylamino)-1-propanesulfonic" should be --(TES), (3-cyclohexylamino)-1-propanesulfonic--.

In Column 7, line 13, "concentraions" should be --concentrations--.

In Column 8, line 58, "(650" should be --@ 650--.

In Column 8, line 59, "(pH" should be --@ pH--.

In Column 10, lines 60-61, (claim 24), delete "to provide a direct reading".

Signed and Sealed this

Twenty-first Day of July, 2009

JOHN DOLL  
*Acting Director of the United States Patent and Trademark Office*